US010088491B2

(12) United States Patent
Valdez et al.

(10) Patent No.: US 10,088,491 B2
(45) Date of Patent: *Oct. 2, 2018

(54) METHODS FOR THE SELECTIVE SEQUESTRATION OF ALKYNE-PRESENTING MOLECULES AND RELATED COMPOSITIONS AND METHODS

(71) Applicant: LAWRENCE LIVERMORE NATIONAL SECURITY, LLC, Livermore, CA (US)

(72) Inventors: Carlos A. Valdez, San Ramon, CA (US); Alexander K. Vu, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,545

(22) Filed: Mar. 7, 2014

(65) Prior Publication Data

US 2014/0275432 A1 Sep. 18, 2014

Related U.S. Application Data

(60) Provisional application No. 61/790,757, filed on Mar. 15, 2013, provisional application No. 61/790,393, filed on Mar. 15, 2013, provisional application No. 61/790,019, filed on Mar. 15, 2013.

(51) Int. Cl.
| | | |
|---|---|---|
| *G01N 33/18* | (2006.01) | |
| *G01N 33/50* | (2006.01) | |
| *G01N 33/74* | (2006.01) | |
| *G01N 33/53* | (2006.01) | |
| *C08F 112/08* | (2006.01) | |

(52) U.S. Cl.
CPC .......... *G01N 33/743* (2013.01); *C08F 112/08* (2013.01); *G01N 33/1826* (2013.01); *G01N 33/5308* (2013.01); *G01N 33/50* (2013.01)

(58) Field of Classification Search
CPC .. G01N 33/00; G01N 33/1826; G01N 33/487; G01N 33/49; G01N 33/493; G01N 33/50; G01N 33/743
See application file for complete search history.

(56) References Cited

U.S. PATENT DOCUMENTS

| | | | |
|---|---|---|---|
| 2008/0241856 A1 | 10/2008 | Wong et al. | |
| 2009/0297609 A1* | 12/2009 | Shoichet | C08G 63/64 424/489 |
| 2012/0226019 A1* | 9/2012 | Aucagne | C07K 1/006 530/326 |
| 2014/0273250 A1 | 9/2014 | Valdez et al. | |
| 2014/0273274 A1 | 9/2014 | Valdez et al. | |

FOREIGN PATENT DOCUMENTS

GB 1325912 * 8/1973

OTHER PUBLICATIONS

Cassidy et al., Angew. Chem. Int. Ed. 45 (2006) 3154-3157.*
Sletten, E.M. and Bertozzi, C.R. "Bioorthogonal chemistry: fishing for selectivity in a sea of functionality" *Angew Chem Int Ed Engl* (2009) 48, 38, pp. 6974-6998.
Prescher, J.A., et al., "Chemical remodeling of cell surfaces in living animals." *Nature* (2004) vol. 430, pp. 873-877.
Sawa, M., et al., "Glycoproteomic probes for fluorescent imaging of fucosylated glycans in vivo." *Proc Natl Aced Sci USA* (2006) vol. 103, 33, pp. 12371-12376.
Baskin, J.M., et al., "Copper-free click chemistry for dynamic in vivo imaging" *Proc Natl Acad Sci USA* (2007) 104, 43, pp. 16793-16797.
Zhang, L., et al., "Ruthenium-catalyzed cycloaddition of alkynes and organic azides" *J Am Chem Soc* (2005) vol. 27, 46, pp. 15998-15999.
Horiba, J.Y., "A Guide to Recording Fluorescence Quantum Yields" (2002), 6 pgs.
Trupp, S. et al., "A fluorescent water-soluble naphthalimide-based receptor for saccharides with highest sensitivity in the physiological pH range." *Org. Biomol. Chem.* (2006) vol. 4, pp. 2965-2968.
Schneider, C. et al., "Direct sub-ppt detection of the endocrine disruptor ethinylestradiol in water with a chemiluminescence enzyme-linked immunosorbent assay." *Anal. Chim. Acta* (2005) vol. 551, pp. 92-97.
Sivakumar, K. et al., "A Fluorogenic 1,3-Dipolar Cycloaddition Reaction of 3-Azidocoumarins and Acetylenes" *Org. Lett.* (2004) vol. 6, pp. 4603-4606.
Rostovtsev, V. V. et al., "A Stepwise Huisgen Cycloaddition Process: Copper(I)-Catalyzed Regioselective "Ligation" of Azides and terminal alkynes." *Angew. Chem. Int. Ed. Engl.* (2002) vol. 41, pp. 2596-2599.
Tornoe, C. et al., "Peptidotriazoles on Solid Phase: [1,2,3]-triazoles by Regiospecific Copper(I)-Catalyzed 1,3-Dipolar Cycloadditions of Terminal Alkynes to Azides" *J. Org. Chem.* (2002) vol. 67, pp. 3057-3064.
Fery-Forgues, S. et al., "Are Fluorescence Quantum Yields So Tricky to Measure? A Demonstration Using Familiar Stationery Products" *J. Chem. Ed.* (1999) vol. 76, pp. 1260-1264.
Snyder, S. A. et al., "Analytical Methods for Detection of Selected Estrogenic Compounds in Aqueous Mixtures" *Environ. Sci. Technol.* (1999) vol. 33, pp. 2814-2820.
Colborn, T. "Building Scientific Consensus on Endocrine Disruptors" *Environmental Toxicology and Chemistry* (1998) vol. 17(1), pp. 1-2.
Smith, P. A. S. and Hall, J.H. "Kinetic Evidence for the Formation of Azene (Electron-Deficient Nitrogen) Intermediates from Aryl Azides" *J. Am. Chem. Soc.* (1961) vol. 84, pp. 480-485.
Melhuish, W. H. "Quantum Efficiencies of Fluorescence Organic Substances: Effect of Solvent and Concentration of the Fluorescent Solute" *J. Phys. Chem.* (1960) vol. 65, pp. 229-235.
Richardson, S.D., "Water Analysis: Emerging Contaminants and Current Issues" *Anal. Chem.* (2009) vol. 81, pp. 4645-4677.
Hanaoka, K., et al., "Design and Synthesis of a Highly Sensitive Off-On Fluorescent Chemosensor for Zinc Ions Utilizing Internal Charge Transfer" *Chem. Eur. J.* (2010), vol. 16, pp. 568-572.

(Continued)

*Primary Examiner* — Roberto Rabago
(74) *Attorney, Agent, or Firm* — Steinfl + Bruno, LLP

(57) ABSTRACT

Provided herein are methods for sequestering an alkyne-presenting molecule in a sample and related sequestration reagents, compositions, methods and systems.

27 Claims, 7 Drawing Sheets

(56) References Cited

OTHER PUBLICATIONS

Martinez, N.A. et al., "Modified Paramagnetic Beads in a Microfluidic System for the Determination of Ethinylestradiol (EE2) in River Water Samples" *Biosensors and Bioelectronics*, vol. 25 (2010), pp. 1376-1381.
Hannah, R., et al., "Exposure Assessment of 17α-Ethinylestradiol in Surface Waters of the United States and Europe" *Environmental Toxicology and Chemistry* (2009) vol. 28(12), pp. 2725-2732.
Van Berkel, G.J., et al. "Deprivation for Electrospray Ionization Mass Spectrometry. 3. Electrochemically Ionizable Derivatives." Anal. Chem., vol. 70, pp. 1544-1554. 1998.
Higashi, T. et al. "Derivatization of neutral steroids to enhance their detection characteristics in liquid chromatography-mass spectrometry." Anal Bioanal Chem., vol. 378, pp. 872-882. 2004.
Ternes, T.A. et al. "Determination of Estrogens in Sludge and Sediments by Liquid Extraction and GC/MS/MS." Anal. Chem., vol. 74, pp. 3498-3504. 2002.
Thompson, A. S. et al. "Direct Conversion of Activated Alcohols to Azides Using Diphenyl Phosphorazidate. A Practical Alternative to Mitsunobu Conditions." J. Org. Chem., vol. 58, pp. 5886-5888. 1993.
Cassidy, M.P. et al. "Practical Synthesis of Amides from In Situ Generated Copper (I) Acetylides and Sulfonyl Azides." Angew. Chem. Int. Ed., vol. 45, pp. 3154-3157. 2006.
Danheiser, R.L. et al. "An Improved Method for the Synthesis of a α-Diazo Ketones." J. Org. Chem., vol. 55(6), pp. 1959-1964. 1990.
Shved, N. et al. "Environmentally Relevant Concentrations of 17α-Ethinylestradiol (EE2) Interfere With the Growth Hormone (GH)/Insulin-Like Growth Factor (IGF)-I Systems in Developing Bony Fish." Toxicological Science, vol. 106(1), pp. 93-102. 2008.
Seiwert, B. and Karst, U. "Ferrocene-based derivatization in analytical chemistry." Anal Bioanal Chem., vol. 390, pp. 181-200. 2008.
Fukuzawa, S. et al. "ClickFerrophos: New Chiral Ferrocenyl Phosphine Ligands Synthesized by Click Chemistry and the Use of Their Metal Complexes as Catalysts for Asymmetric Hyrdogenation and Allylic Substitution." Organic Letter, vol. 9(26), pp. 5557-5560. 2007.
Quirke, J.M.E. et al. "Ferrocene-Based Electroactive Derivatizing Reagents for the Rapid Selective Screening of Alcohols and Phenols in Natural Product Mixtures Using Electrospray-Tandem Mass Spectrometry." J. Nat. Prod., vol. 63, pp. 230-237. 2000.
Kuch, H. M. et al. "Determination of Endocrine-Disrupting Phenolic Compounds and Estrogens in Surface and Drinking Water by HRGC-(NCI)-MS in the Picogram per Liter Range." Environ. Sci. Technol. vol. 35, pp. 3201-3206. 2001.
Barnett, S.M. et al. Surface-Enhanced Raman Scattering Spectroscopic Study of 17α Ethinylestradiol on Silver Colloid and in Glass-Deposited Ag-I 7a-Ethinylestradiol Film. Anal.Chem., vol. 66, pp. 1762-1765. 1994.
Van Berkel, G.J. et al. "Preforming Ions in Solution via Charge-Transfer Complexation for Analysis by Electrospray Ionization Mass Spectrometry." Anal. Chem., vol. 63 (18), pp. 2064-2068. 1991.
Balli et al. "Synthese von 1-Athyl-2-azido-6-X-chinolinium-fluoroboraten" Helvetica Chimica Acta; 1970; vol. 53; No. 7; pp. 1903-1912—English Abstract Only + Full German text.
Sezer et al. "Transdiazotization of Acylacetaldehydes in Neutral-to-Acidic Medium. A Direct Approach to the Synthesis of α-Diazo-β-oxoaldehydes)" Helvetica Chimica Acta; 1994; vol. 77; pp. 2323-2334.
Szanti-Pinter et al. "Synthesis of ferrocene-labelled steroid derivatives via homogenous catalytic methods" Journal of Organometallic Chemistry; 2012; vol. 718; pp. 105-107.
Szanti-Pinter et al. "Synthesis of steroid-ferrocene conjugates of steroidal 17-carboxamides via a palladium-catalyzed aminocarbonylation—Copper-catalyzed azide-alkyne cycloaddition reaction sequence" Steroids; 2011; vol. 76; pp. 1377-1382.
Upton et al. "Synthesis of ferrocene-functionalized monomers for biodegradable polymer formation" Inorg. Chem. Front.; 2014; vol. 1; pp. 271-277.
Sigma-Aldrich, Excerpt from "Resins for Solid-Phase Synthesis" retrieved from http://web.archive.org/web/20120629084629/http://www.sigmaaldrich.com/chemistry/drug-discovery/resin-explorer/solid-phase-resins.html on Jan. 12, 2017. 1 page.
Fluka, Resins for solid-phase Peptide Synthesis, vol. 3, No. 4, 2003, 32 pages.
Field, J., et al. "Fate of Alkylbenzenesulfonates and Dialkyltetralinsulfonates in Sewage-Contaminated Groundwater" Environ. Sci. Technol., 26, 1992. pp. 1140-1148.
Non-Final Office Action issued for U.S. Appl. No. 14/201,480, filed Mar. 7, 2014 on behalf of Lawrence Livermore National Security, LLC. dated May 19, 2017. 12 pages.
Non-Final Office Action issued for U.S. Appl. No. 14/201,530, filed Mar. 7, 2014 on behalf of Lawrence Livermore National Security, LLC. dated Jan. 25, 2017. 19 pages.
Notice of Allowance issued for U.S. Appl. No. 14/201,530, filed Mar. 7, 2014 on behalf of Lawrence Livermore National Security, LLC. dated Jun. 28, 2017. 11 pages.
Restriction Requirement issued for U.S. Appl. No. 14/201,480, filed Mar. 7, 2014 on behalf of Lawrence Livermore National Security, LLC. dated Sep. 9, 2016. 10 pages.
Restriction Requirement issued for U.S. Appl. No. 14/201,530, filed Mar. 7, 2014 on behalf of Lawrence Livermore National Security, LLC. dated Sep. 1, 2016. 10 pages.
Tian, H., et al. "Micelle-induced multiple performance improvement of fluorescent probes for H2S detection", Analytica Chimica Acta 768, 2013. pp. 136-142.

* cited by examiner

METHODS FOR THE SELECTIVE SEQUESTRATION OF ALKYNE-PRESENTING MOLECULES AND RELATED COMPOSITIONS AND METHODS

CROSS REFERENCE TO RELATED APPLICATIONS

The present application claims priority to U.S. Provisional Application 61/790,757 entitled "Methods for The Selective Sequestration of Alkyne-Presenting Molecules and Related Compositions and Systems" filed on Mar. 15, 2013, to U.S. Provisional Application 61/790,019 entitled "Methods for The Selective Detection of Alkyne-Presenting Molecules and Related Compositions and Systems" filed on Mar. 15, 2013, and to U.S. Provisional Application 61/790,393 entitled "Methods for The Selective Detection of Alkyne-Presenting Molecules and Related Compositions and Systems" filed on Mar. 15, 2013, each of which is herein incorporated by reference in their entirety. This application may be related to U.S. Non-Provisional application Ser. No. 14/201,530, U.S. Pat. No. 9,791,463, and entitled "Methods for The Selective Detection of Alkyne-Presenting Molecules and Related Compositions and Systems" filed on Mar. 7, 2014 and to U.S. Non-Provisional application Ser. No. 14/201,480 and entitled "Methods for The Selective Detection of Alkyne-Presenting Molecules and Related Compositions and Systems" filed on Mar. 7, 2014, each of which is herein incorporated by reference in their entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to methods for sequestration of alkyne-presenting molecules, and in particular 17α-ethinylestradiol, and related compositions and systems.

BACKGROUND

Sequestration of alkyne-presenting molecules, such as 17α-ethinylestradiol and other steroid-based contaminants, in the environment, particularly in water systems, has become an issue of utmost importance due to the toxic effects exerted by these chemical species in biological systems even at very low concentrations.

However, specific and selective sequestration of those compounds can be challenging also in view of the fact that several synthetic and natural chemicals possess the ability to mimic hormones and as such are able to interfere or disrupt hormonal homeostasis in biological systems.

Accordingly, despite the fact that several methods and systems for sequestration of alkyne-presenting molecules, and in particular 17α-ethinylestradiol, are available, performance of an accurate and selective sequestration remains challenging.

SUMMARY

Described herein are methods and related compositions and systems that in some embodiments can be used in the selective sequestration of steroids, and in particular, the selective sequestration of alkyne presenting molecules, and in particular 17α-ethinylestradiol.

According to a first aspect, a method and system for selectively sequestering one or more alkyne-presenting molecule from an unprepared matrix is described, the method comprising: contacting a sequestration reagent with the unprepared matrix for a time and under a condition to allow binding of the sequestration reagent the one or more alkyne-presenting molecules possibly present in the matrix to the sequestration reagent thus sequestering the alkyne-presenting molecules from the unprepared matrix. In the method, the sequestration reagent comprises a support presenting one or more azide or sulfonyl azide groups, wherein binding of the azide or sulfonyl azide groups to the one or more alkyne-presenting molecules results in sequestration of the alkyne-presenting molecules from the matrix. The system comprises at least one of one or more a sequestration reagents herein described, a reagent for the azide or sulfonyl azide group reactions and/or a copper(I) source for the simultaneous, combined, or sequential use in the method herein described.

According to a second aspect, a sequestration reagent is described, the sequestration reagent comprising: a support presenting one or more azide or sulfonyl azide groups. In some embodiments, the support is an organic polymer moiety. In some embodiments, the one or more binding moieties are azide groups or sulfonyl azide groups.

The methods and related compositions and systems described herein in several embodiments allow the selective sequestration of alkyne-presenting molecules, 17α-ethinylestradiol, from unprepared aqueous and organic matrices.

The methods and related compositions and systems described herein in several embodiments can be used, for example, for the sequestration of the alkyne-presenting molecules, such as contraceptive pill's active ingredient 17-α-ethinylestradiol (EE2), in various unprepared water matrices and organic media using the technique of fluorescence spectroscopy. Furthermore, application of these methods and related compositions and systems can be extended, for example, to EE2 sequestration in blood and urine samples that can become important if removal systems are to be developed for individuals consuming the drug. No previous uses of this technology (sequestration of EE2) have been described for this specific application.

The methods and related compositions and systems described herein in several embodiments can be used, for example, for the removal of the contraceptive pill's active ingredient 17-α-ethinylestradiol (EE2) from various water matrices and organic media using the Cu(I)-catalyzed 1,3-dipolar cycloaddition reaction commonly known as "click chemistry". Furthermore, application of these methods and related compositions and systems can be extended to the building of purification devices that possess the azido-functionality and thus are able to directly interact with alkyne-presenting molecules such as EE2 without the need for sample preparation.

The details of one or more embodiments of the disclosure are set forth in the accompanying drawings and the description below. Other features and objects will be apparent to a skilled person from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
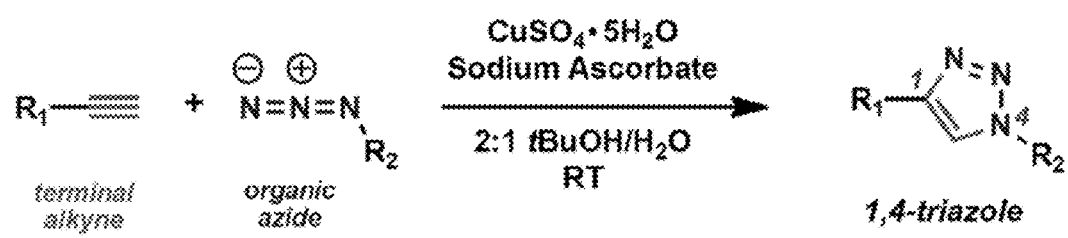
FIG. 1 shows a schematic of The Cu(I)-catalyzed Azide-Alkyne Dipolar Cycloaddition reaction (Click chemistry). Note that the product is a 1,4-substituted triazole ring joining species $R_1$ and $R_2$.
Figure 2:
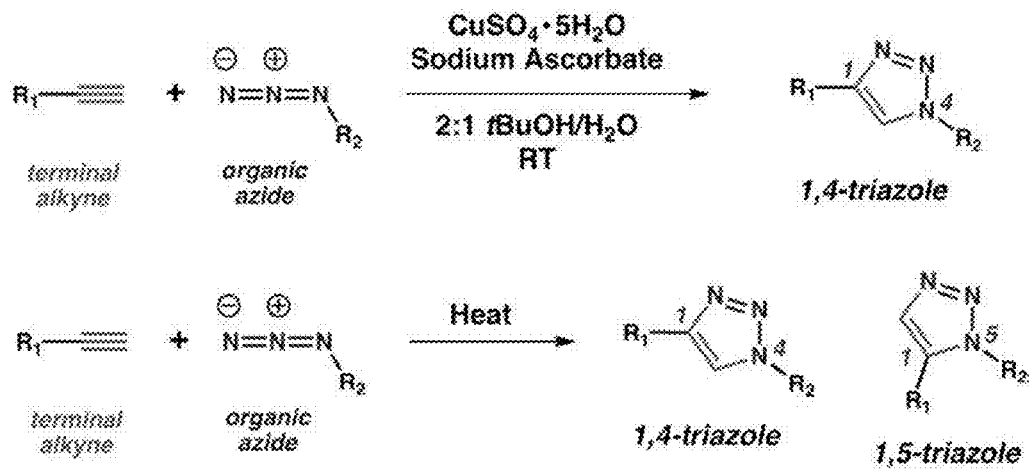
FIG. 2 shows a schematic of the Cu(I)-catalyzed Azide-Alkyne Cycloaddition (CuAAC) reaction to produce a 1,4-substituted triazole ring joining species R1 and R2, whereas the original, thermal addition of the azide and the alkyne yields the 1,5-substituted product in addition to the 1,4-substituted adduct.
Figure 3:
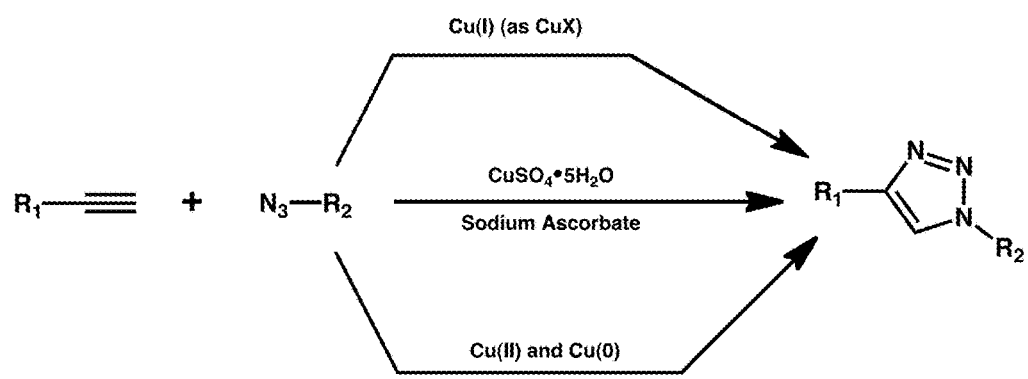
FIG. 3 shows Click chemistry catalyzed by various sources of Cu(I) ions, a) Cu(I) salts; b) Cu(I) from the $CuSO_4$/sodium ascorbate system and c) Cu(I) originating from the Cu(0)/Cu(II) comproportionation reaction as described herein.
Figure 4:
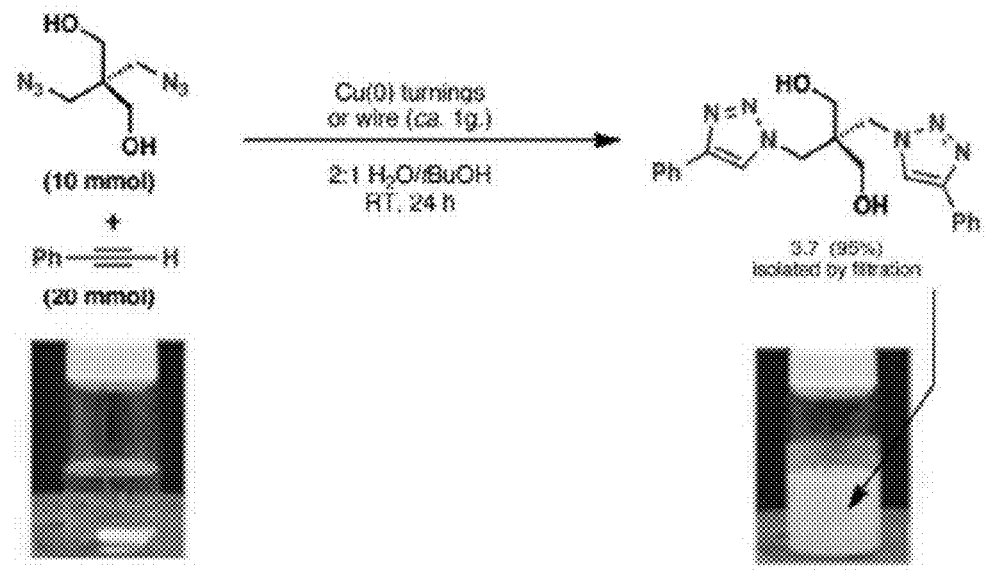
FIG. 4 shows a schematic and image of an exemplary click chemistry reaction using a copper wire as the sole source of catalytic Cu(I) (Fokin group).

Described herein are methods and related compositions and systems that in some embodiments can be used in the selective sequestration of alkyne-presenting molecules, and in particular, the selective sequestration of alkyne presenting molecule, and in particular 17α-ethinylestradiol.

The term "alkyne presenting molecule" as used herein indicates a molecule presenting a alkyne group for binding. The term "present" as used herein with reference to a compound or functional group indicates attachment performed to maintain the chemical reactivity of the compound or functional group as attached. Accordingly, an alkyne group presented on a molecule, is able to perform under the appropriate conditions the one or more chemical reactions that chemically characterize the alkyne group including click chemistry. In particular, an alkyne group can be included in an alkyne presenting molecule in any position and configuration as long as the alkyne group is presented in the molecule for binding or be subjected to other reactions.

In some embodiments herein described, the alkyne presenting molecule comprises a terminal alkyne. Exemplary molecule wherein the alkyne presenting molecule comprises a terminal alkyne include, for example, 17α-ethinylestradiol, acetylene, propyne, norethynodrel, rasagiline, and others identifiable to a skilled person.

In some embodiments herein described the alkyne presenting molecule comprises an internal alkyne group. Exemplary molecule wherein the alkyne presenting molecule comprises an internal alkyne include, for example, terbinafine, cicutoxin, oenanthotoxin, falcarinol, efavirenz, calicheamicin, tariric acid, and others identifiable to a skilled person.

In particular, in some embodiments, the methods and related compositions and systems can be used in the selective sequestration of alkyne-presenting molecules, and in particular 17α-ethinylestradiol, from unprepared aqueous and organic matrices.

The term "sequestration", as used herein, refers to the removal of a substance from a medium by way of attaching the substance to be removed to a sequestration reagent when the sequestration reagent comes in contact with the substance to be removed. The term "sequestration reagent" refers to a substance capable of attaching another substance to itself thus forming a sequestration reagent-substance adduct. In some embodiments, the sequestering of a substance is accomplished by the formation of one or more bonds (e.g. covalent, dative, ionic, or other known to a skilled person) between groups on the sequestration reagent and groups on the substance to be removed.

In particular and by way of example, in some embodiments, bonds can be formed by the reaction between an azide group on the sequestration reagent and an alkyne on the substance to be removed to form a triazole moiety thus covalently linking the substance to be removed to the sequestration reagent by way of the triazole through a Hüisgen reaction as herein described.

In particular, and by way of another example, in some embodiments, bonds can be formed by the reaction between a sulfonyl azide (a sulfur-based rather than a carbon-based azide) on the sequestration reagent and a terminal alkyne on the substance to be removed to form an N-acylsulfonamide thus covalently linking the substance to be removed to form a triazole moiety thus covalently linking the substance to be removed to the sequestration reagent by way of the N-acylsulfonamide as herein described.

The terms "matrix", and plural "matrices", as used herein, refers to a medium in which a particular substance of interest (e.g. a substance to be removed or detected) is dispersed. In some embodiments, the matrix can be an aqueous or organic solution containing a particular substance of interest. In particular, exemplary aqueous and organic matrices can include, blood, urine, drinking water, agricultural irrigation water and others identifiable to a skilled person upon a reading of the present disclosure.

In particular, in some embodiments, the matrix is an unprepared matrix. The term "unprepared matrix" as used herein refers to a matrix that has not been subjected to matrix preparation, wherein the term "matrix preparation" refers to the way a matrix is treated prior to its contact with a sequestration reagent to introduce an azide ($—N_3$) group or alkyne group into a molecule (e.g., by incorporating an azide- or alkyne-bearing sugar or amino acid into a biomolecule; see, e.g. [Ref 1-4]) for binding to a sequestration reagent through "click chemistry" as described herein, and other sample preparations that would be apparent to a skilled person upon a reading of the present disclosure. In particular, in some instances absence of matrix preparation in the sense of the present disclosure can result in a method wherein reacting an azide presenting molecule with the alkyne presenting molecule is performed without any information beforehand as to the quantity, concentration, or chemical reactivity of the compound presenting the alkyne group, and possibly also the chemical composition of the medium when the reaction is expected to occur.

Accordingly, according to some embodiments of the disclosure, the amount of azide or alkyne in a molecule to be detected, and thus the amount of molecule to be detected (e.g. an alkyne-presenting molecule) is not known beforehand in the unprepared matrices herein described.

In particular, in some embodiments, the method for selective sequestration of alkyne-presenting molecules, and in particular 17α-ethinylestradiol, from an unprepared aqueous or organic matrix comprises: contacting a sequestration reagent with the unprepared matrix for a time and under a condition to allow binding of the sequestration reagent the one or more alkyne-presenting molecules possibly present in the unprepared matrix to the sequestration reagent thus sequestering the alkyne-presenting molecules from the unprepared matrix. In particular, in some embodiments, the sequestration reagent comprises a support presenting one or more azide or sulfonyl azide groups, wherein binding of the azide or sulfonyl azide groups to the one or more 17α-ethinylestradiol molecules results in sequestration of the 17α-ethinylestradiol molecules from the unprepared matrix.

In embodiments in which the alkyne is a terminal alkyne, sequestration according to embodiments herein described can be performed by contacting the unprepared matrix with a sequestration reagent presenting an azide group to allow reaction of the alkyne group with the azide group through click chemistry. In some of those embodiments, the reaction can be performed can be performed as herein described at room temperature or up to temperatures of between approximately 40-60° C. or of up to temperatures of 100° C. A skilled person can choose the temperature by considering, for example, the thermal stability of the label organic moiety presenting an azide group (e.g. if the label organic moiety presenting an azide group is an aryl azide, the temperature can be kept below 60° C. or other temperature suitable to prevent thermal decomposition of the label organic moiety presenting an azide). In particular, in those embodiments in which the alkyne is an internal alkyne and the temperature is to be maintained below approximately 60° C., a catalysts such as a ruthenium-based catalyst (e.g., Cp*RuCl(PPh$_3$)$_2$) can be used in place of Cu(I) to perform the reaction (see, e.g., [Ref 5]). In addition, in those embodiments in which the alkyne is a terminal alkyne, the amount of Cu(I) as herein described can be 5-20 mol % relative to the alkyne component or up to 50 mol % or up to stoichiometric amounts. In addition, in those embodiments in which the alkyne is a terminal alkyne, the amount of ascorbic acid used as herein described can be in excess amounts.

In embodiments in which the alkyne is an internal alkyne sequestration according to embodiments herein described can be performed by contacting the unprepared matrix with a sequestration reagent presenting an azide group to allow reaction of the alkyne group with the azide group through click chemistry. In some of those embodiments, the reaction can be performed at to temperatures of between approximately 40-60° C. or of up to temperatures of 100° C. or higher. A skilled person can choose the temperature by considering, for example, the thermal stability of the label organic moiety presenting an azide group (e.g. if the label organic moiety presenting an azide group is an aryl azide, the temperature can be kept below 60° C. or other temperature suitable to prevent thermal decomposition of the label organic moiety presenting an azide; or if the label organic moiety presenting an azide group is an alkyl azide, the temperature can be above 100° C. and in particular at a temperature above 100° C. suitable to prevent thermal decomposition of the label organic moiety presenting an azide). In particular, in those embodiments in which the alkyne is an internal alkyne and the temperature is to be maintained below approximately 60° C., a catalysts such as a ruthenium-based catalyst (e.g., Cp*RuCl(PPh$_3$)$_2$) can be used in place of Cu(I) to perform the reaction (see, e.g., [Ref 5]). In addition, in those embodiments in which the alkyne is an internal alkyne, the amount of Cu(I) as herein described can be 5-20 mol % relative to the alkyne component or up to 50 mol % or up to stoichiometric amounts. In addition, in those embodiments in which the alkyne is an internal alkyne, the amount of ascorbic acid used as herein described can be in excess amounts.

The term "support" as used herein refers to a non-reactive structure presenting a reactive group capable of performing the sequestration as herein described. In particular, in some embodiments, the support can be a cross-linked organic polymer such as, for example a polymeric resin (e.g. trityl resin, Wang resin, Rink amide and chloromethylphenyl polystyrene resins, and others that would be apparent to a skilled person upon a reading of the present disclosure). In other embodiments, the support can be an inorganic structure such as glass, silica gel, zeolite, or other inorganic structure identifiable to a skilled person upon a reading of the present disclosure.

In some embodiments, the sequestration reagent adapted to selectively bind to one or more alkyne-presenting molecules, and in particular 17α-ethinylestradiol molecules, possibly present in the matrix is adapted to comprise one or more azide functional groups. In other embodiments, the sequestration reagent adapted to selectively bind to one or more 17α-ethinylestradiol molecules possibly present in the matrix is adapted to comprise one or more sulfonyl azide functional groups.

In particular, in embodiments where the sequestration reagent is adapted to comprise one or more azide or sulfonyl azide groups, the azide and sulfonyl azide groups are capable of selective reaction with the alkyne of 17α-ethinylestradiol to form triazoles and N-acylsulfonamides, respectively.

In particular, in some embodiments, sequestration reagent has formula XXXV:

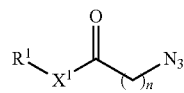

XXXV wherein: $R^1$ is a cross-linked organic polymer; $X^1$ is selected from the group consisting of O, N, and S; and n is between 4 and 7.

In particular, in some embodiments, the cross-linked organic polymer group $R^1$ can be a polymeric resin (e.g., such as that used in solid-phase peptide synthesis) possessing reactive functional groups such that they can be reacted with azidocarboxylic acids so as to produce sequestration reagents of Formula XXXV (see, e.g., Example 1). By way of example, such polymeric resins can include resins such as those used in solid-phase peptide synthesis (see, e.g., [Ref 6]). Exemplary resins include, for example, Wang resins, Rink amide resins, trityl resins chloromethylphenyl polystyrene resins, and others identifiable to a skilled person upon a reading of the present disclosure.

In particular, in other embodiments, $R^1$ in Formula XXXV can comprise a trialkoxysilyl-substituted alkyl or aryl group which can be used to attach the sequestration reagent to an inorganic support such as glass or silica gel.

In some embodiments, the selective sequestration of alkyne-presenting molecules, and in particular 17α-ethinylestradiol, from an aqueous or organic matrix is performed by the contacting the sequestration reagent with the matrix for a time and under a condition so as to bind one or more alkyne-presenting molecules possibly present in the matrix to the sequestration reagent thus sequestering the alkyne-presenting molecules from the matrix.

In particular, in some embodiments, the contacting can be performed by dispersing the sequestration reagent in the matrix in combination with a copper(0), copper(I) and/or copper(II) compound providing a copper(I) source to provide a mixture; and tumbling the mixture. In other embodiments, the contacting can be performed by passing the matrix through a container (e.g. a cartridge or column) containing the sequestration reagent and with a copper(0), copper(I) and/or copper(II) compound providing a copper (I).

In particular, in some embodiments, the selective sequestration of alkyne-presenting molecules can also be coupled with detection of the sequestration of the alkyne-presenting molecules. In particular, in some embodiments, the coupling of sequestration and detection can be achieved by performing the contacting with a sequestration reagent as herein described, wherein the sequestration reagent further comprises detection reagents comprising fluorescent or pre-fluorescent moieties such as those of U.S. Provisional Application 61/790,019 and U.S. Non-Provisional application Ser. No. 14/201,530, U.S. Pat. No. 9,791,463, and entitled "Methods for The Selective Detection of Alkyne-Presenting Molecules and Related Compositions and Systems" filed on Mar. 7, 2014.

In particular, in some embodiments, the comprising of a detection reagent in the sequestration reagent can be accomplished by attaching a detection reagent comprising fluorescent or pre-fluorescent moieties through functional groups on the substituents on the fluorescent or pre-fluorescent moieties to the support of the sequestration reagent. For example, if the support is a polymeric resin (e.g. such as that used in solid phase peptide synthesis) comprising amine groups, then the detection reagents comprising fluorescent or pre-fluorescent moieties can comprise on the fluorescent or pre-fluorescent moieties, for example, $C_1$-$C_8$ alkyl substituted with a carboxylic acid which can be attached to the amine groups of the polymeric resin (for example by converting the carboxylic acid to an acid chloride or by using peptide synthesis techniques known to a skilled person) through amide bonds.

In some embodiments, the coupling of detection and sequestration of alkyne-presenting molecules can allow detection of the sequestration. For example, when the detection reagent attached to the sequestration reagent becomes fluorescent only upon covalently bonding to an alkyne-presenting moiety, the sequestration of the alkyne-presenting moiety can be detected by the sequestration reagent becoming fluorescent upon the sequestration of the alkyne-presenting molecule thus indicating that the sequestration has occurred. In some embodiments, the amount of fluorescence can indicate the amount of alkyne-presenting molecule sequestered.

In some embodiments, the systems herein described can be provided in the form of kits of parts. In a kit of parts, one or more sequestration reagents and copper(I) sources can be comprised in the kit independently. In particular, in some embodiments, the copper(I) source can be a Cu(I) salt (e.g. CuCl or CuBr). In other embodiments, the copper(I) source can be a Cu(II) salt (e.g. $CuSO_4$) that can be combined with a reducing agent (e.g. ascorbic acid) to provide Cu(I) ions. In other embodiments, the copper(II) source can be a mixture of Cu(0) and Cu(II) sources that can react through comproportionation to provide Cu(II) ions. In other embodiments, the kit of parts can further comprise a reducing agent (e.g. ascorbic acid) to prevent oxidation of the Cu(I) source.

In particular, also described herein are sequestration reagents for the selective sequestration of alkyne-presenting molecules, and in particular 17α-ethinylestradiol. In particular, in some embodiments, the sequestration reagent comprises a support presenting one or more azide or sulfonyl azide groups.

In particular, in some embodiments, the sequestration reagent has a structure according to formula XXXVI:

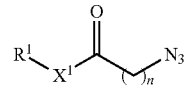

XXXVI $R^1$ is a cross-linked organic polymer; $X^1$ is selected from the group consisting of O, N, and S; and n is between 4 and 7.

In particular, in some embodiments, the cross-linked organic polymer group R/can be a polymeric resin (e.g., such as that used in solid-phase peptide synthesis) possessing reactive functional groups such that they can be reacted with azidocarboxylic acids so as to produce sequestration reagents of Formula XXXVI (see, e.g., Example 1). By way of example, such polymeric resins can include resins such as those used in solid-phase peptide synthesis (see, e.g., [Ref 6]). Exemplary resins include, for example, Wang resins, Rink amide resins, trityl resins chloromethylphenyl polystyrene resins, and others identifiable to a skilled person upon a reading of the present disclosure.

In particular, in other embodiments, $R^1$ in Formula XXXVI can comprise a trialkoxysilyl-substituted alkyl or aryl group which can be used to attach the sequestration reagent to an inorganic support such as glass or silica gel.

In some embodiments, R1 in Formula XXXVI can further comprise detection reagents comprising fluorescent or pre-fluorescent moieties such as those of U.S. Provisional Application 61/790,019 and U.S. Non-Provisional application Ser. No. 14/201,530, U.S. Pat. No. 9,791,463, and entitled "Methods for The Selective Detection of Alkyne-Presenting Molecules and Related Compositions and Systems" filed on Mar. 7, 2014.

In particular, in some embodiments, the comprising of a detection reagent in the sequestration reagent can be accomplished by attaching a detection reagent comprising fluorescent or pre-fluorescent moieties through functional groups on the substituents on the fluorescent or pre-fluorescent moieties to the support of the sequestration reagent. For example, if the support is a polymeric resin (e.g. such as that used in solid phase peptide synthesis) comprising amine groups, then the detection reagents comprising fluorescent or pre-fluorescent moieties can comprise on the fluorescent or pre-fluorescent moieties, for example, $C_1$-$C_8$ alkyl substituted with a carboxylic acid which can be attached to the amine groups of the polymeric resin (for example by converting the carboxylic acid to an acid chloride or by using peptide synthesis techniques known to a skilled person) through amide bonds.

Described herein are methods and related compositions and systems that in some embodiments can be used in the selective sequestration of steroids, and in particular, the selective sequestration of 17α-ethinylestradiol.

In some embodiments, the sequestered 17α-ethinylestradiol or other alkyne presenting molecule can be detected on the support of in solution following cleavage of the molecule from the support, by mass spectrometry, Nuclear Magnetic Resonance spectroscopy, infrared spectroscopy and/or additional techniques and approaches identifiable by a skilled person.

In particular, in some embodiments, the detection by mass spectrometry can be accomplished by performing the sequestration of alkyne-presenting moieties by methods described herein with sequestration reagents as described herein, wherein the sequestration reagents further comprise one or more moieties capable of being detected by mass spectrometry, such as, for example, the ferrocenyl, pyridinium, and other moieties of U.S. Provisional Application 61/790,393 and U.S. Non-Provisional application Ser. No. 14/201,480 and entitled "Methods for The Selective Detection of Alkyne-Presenting Molecules and Related Compositions and Systems" filed on Mar. 7, 2014.

In some embodiments, the comprising of one or more moieties capable of being detected by mass spectrometry in the sequestration reagents can be achieved by attaching, as described herein, a detection reagent comprising fluorescent or pre-fluorescent moieties through functional groups on the substituents on the fluorescent or pre-fluorescent moieties to the support of the sequestration reagent, wherein the substituents on the fluorescent or pre-fluorescent moieties further comprise the moieties capable of being detected by mass spectrometry. For example, when one of the substituents of the fluorescent or pre-fluorescent moieties is a $C_1$-$C_8$ alkyl substituted with an amine, the amine can be coupled to the carbonyl group of ferrocenecarboxylic acid (for example by converting the carboxylic acid to an acid chloride or by using peptide synthesis techniques known to a skilled person).

Further characteristics of the present disclosure will become more apparent hereinafter from the following detailed disclosure by way or illustration only with reference to an experimental section.

EXAMPLES

The methods for the selective sequestration of 17α-ethinylestradiol and related compositions and systems herein described are further illustrated in the following examples, which are provided by way of illustration and are not intended to be limiting.

Example 1: Synthesis of Trityl-Based Azido PS Resin

Figure 10:
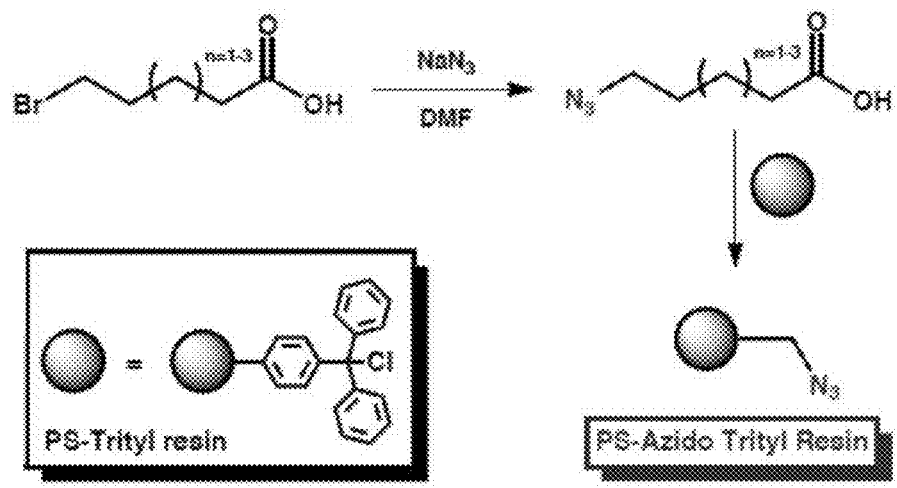
FIG. 10 shows a schematic of an exemplary synthesis of azido-containing acid and PS-azido trityl resin according to embodiments herein described.

Azido-modified resins that are to be used in the sequestering approach according to embodiments herein described can be synthesized in an efficient manner. Thus, the syntheses can be not only reliable but composed of the minimal amount of steps along the way so as to reduce the need of time-spending purifications. By way of example, a trityl-based system can be selected, for example, due to its ubiquitous presence in the realm of solid phase synthesis where its chemistry and protocols for its handling are well-documented. By way of example, the synthesis of a azido linker that can be attached to the resin is shown in FIG. 10 (is this figure the same as FIG. 10). For this linker the core of the aliphatic carboxylic acid, pentanoic acid can be chosen because its 5-bromo derivative is commercially available. Meaningful interactions with substrates can be achieved by selection of a linker of appropriate length. For example, the carboxylic acids, hexanoic and heptanoic acid, have desirable lengths.

The synthesis of the 5-azidopentanoic acid is achieved by heating 5-bromopentanoic acid in the presence of sodium azide (FIG. 10). This acid, after purification, can be posed for the resin's modification. It is important to highlight that any resin could be modified with a azide-bearing functionality and as such it would be used in the EE2-sequestering technologies described in this disclosure. Thus, other resins include: Merrifield, Wang and Rink amide resins and their modified versions thereof.

Figure 5:
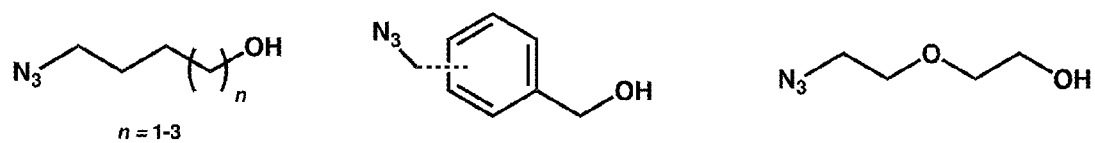
FIG. 5 shows exemplary alternate linkers that can be employed in the resin's modification according to embodiments herein described.
Figure 6:
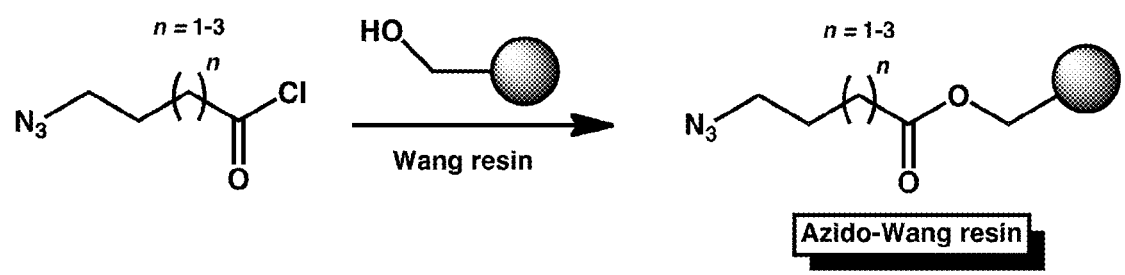
FIG. 6 shows a schematic of an exemplary synthesis of Azido Wang resin according to embodiments herein described.
Figure 7:
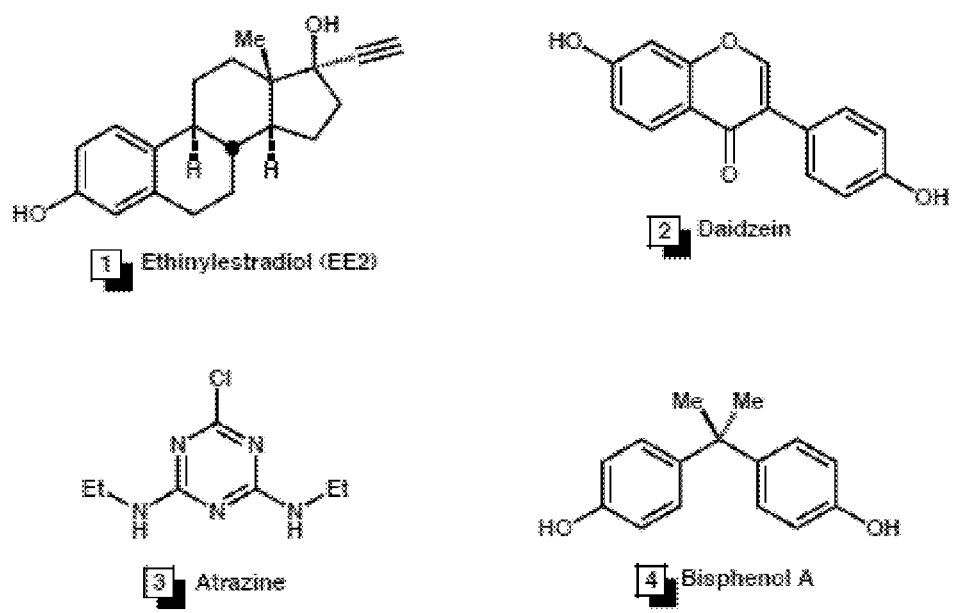
FIG. 7 shows exemplary Endocrine Disrupting Compounds (EDCs).
Figure 8:
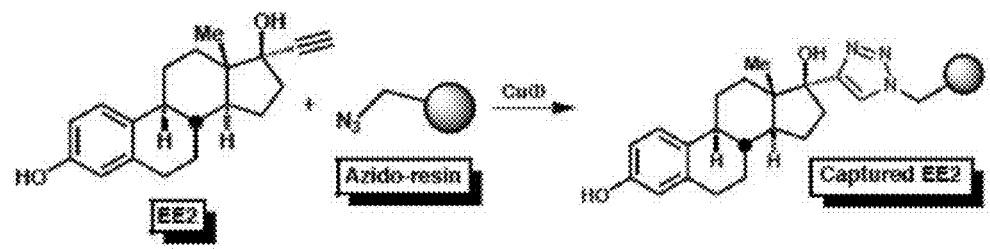
FIG. 8 shows a schematic of the overall strategy described in embodiments herein for the sequestration of EE2 from mixtures (e.g., aqueous or organic mixtures).
Figure 9:
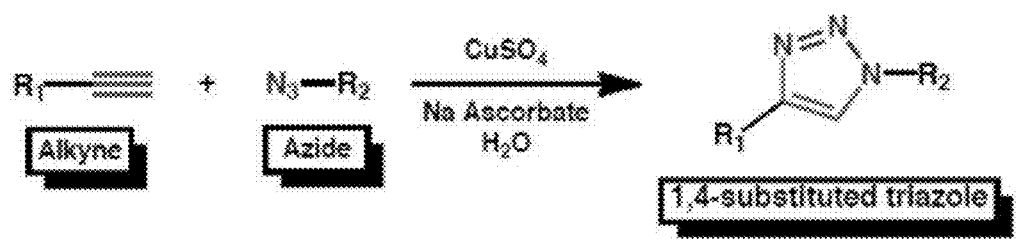
FIG. 9 shows a schematic of an exemplary Cu(I)-catalyzed Azide-Alkyne Cycloaddition (CuAAC) reaction in an aqueous medium. Note that the product is a 1,4-substituted triazole ring joining species R1 and R2, whereas the original, thermal addition of the azide and the alkyne yields the 1,5-substituted product in addition to the 1,4-substituted adduct.

Along the same line of thought, several other linkers can offer other avenues for detection of EE2 once they are attached to the resin. Some of these are presented in FIG. 5. In cases where steric issues are encountered when labeling the resin the reaction time can be extended over 2-3 days to increase efficiency of the labeling. This low level of labeling will eventually translate into poor sequestering capability by the resin.

The resin used in this Example is the commercially available chlorotrityl chloride resin. The first step in preparing the resin for its modification is its swelling in the a suitable solvent such as dichloromethane for 3-4 hours. Since the resin has been swelled, it can be filtered and taken up in anhydrous, solid-phase synthesis grade DMF (N,N-dimethylformamide) or NMP (N-methylpyrrolidinone) where it can be modified with the azido acid. It is worthwhile to point out that the amount of derivatization on the resin can be evaluated at this time so as to know its loading.

Example 2: Application Description

Resins, such as those from Example 1, can be used to sequester EE2 from both, organic and aqueous mixtures due to the CuAAC reaction (Click chemistry) having been proven to work efficiently in both. Furthermore, due to the chemoselective nature of the reaction, it is expected that other species present in the mixture will not interfere with the efficacy of the sequestration. An exemplary schematic of a process for sequestration of EE2 is given in FIG. 11.

Figure 11:
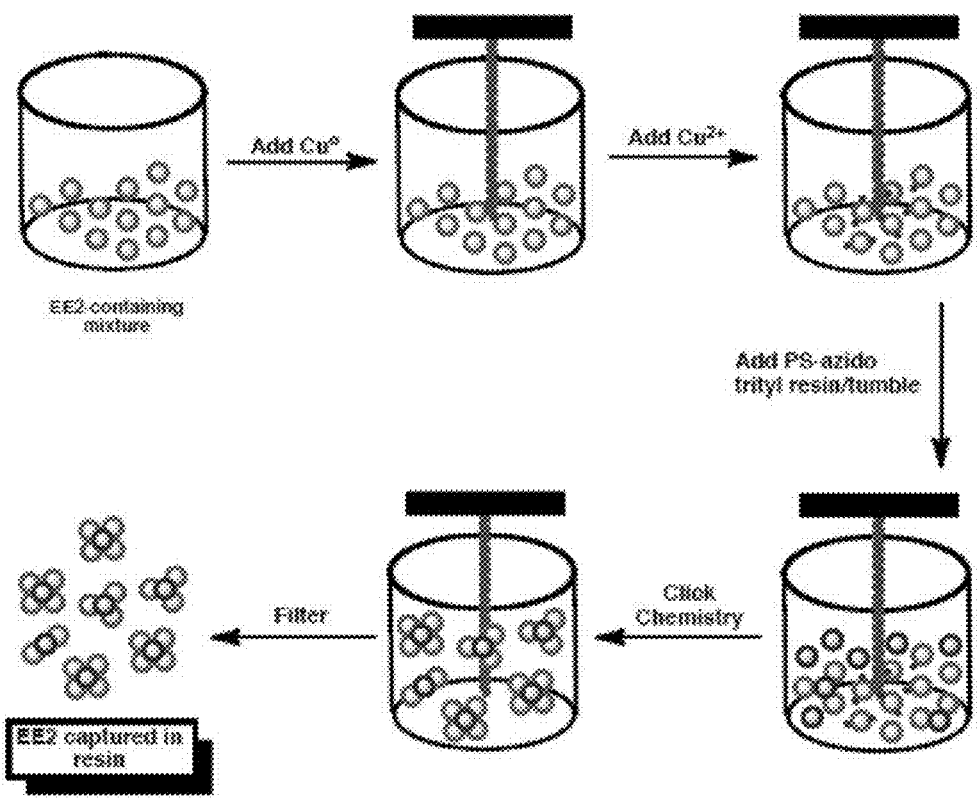
FIG. 11 shows a schematic of an exemplary process for EE2 removal from aqueous and organic mixtures using elemental copper comproportionation according to embodiments herein described.

As shown in FIG. 11, the azido resin can serve as a sequestering entity for the EE2 in a given mixture (aqueous or organic). The elemental copper, which in some embodiments can be a piece of copper wiring or coated on the inside of a container where the treatment can take place, is expected to react with the Cu(II) species to generate the Cu(I) catalyst needed for the EE2 capture onto the resin. The Cu(II) species can come from, for example, the ubiquitous, widely used $CuSO_4$ salt. This salt can be dissolved in water and the characteristic blue solution can be added onto the reservoir to generate the catalytic Cu(I) ions. Only a small amount of Cu(I) ions need to be generated as the process is catalytic in nature. Once these Cu(I) species has been generated, it is a matter of tumbling the resin along with the mixture containing the EE2 to start the reaction. Stirring is expected to cause the resin to break apart, while gentle tumbling will not result in this destruction. Once the reaction has taken place, the resin can be filtered and disposed. For quantification purposes, the EE2 can be cleaved from the resin with acid (e.g. 0.1 TFA in dichloromethane) and thus be able to measure the amount of EE2 that was present in the mixture to begin with. A skilled person will realize that different resins can be cleaved with different conditions depending on the type of resin chosen.

The examples set forth above are provided to give those of ordinary skill in the art a complete disclosure and description of how to make and use the embodiments of the methods for the selective detection of alkyne-presenting molecules and related compositions and systems of the disclosure, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Unless otherwise indicated, the term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

Unless otherwise indicated, the term "hydrocarbyl" as used herein refers to any univalent radical, derived from a hydrocarbon, such as, for example, methyl or phenyl. The term "hydrocarbylene" refers to divalent groups formed by removing two hydrogen atoms from a hydrocarbon, the free valencies of which may or may not be engaged in a double bond, typically but not necessarily containing 1 to 20 carbon atoms, in particular 1 to 12 carbon atoms and more particularly 1 to 6 carbon atoms which includes but is not limited to linear cyclic, branched, saturated and unsaturated species, such as alkylene, alkenylene alkynylene and divalent aryl groups, e.g., 1,3-phenylene, —CH2CH2CH2-propane-1,3-diyl, —CH2-methylene, —CH=CH—CH=CH—. The term "hydrocarbyl" as used herein refers to univalent groups formed by removing a hydrogen atom from a hydrocarbon, typically but not necessarily containing 1 to 20 carbon atoms, in particular 1 to 12 carbon atoms and more particularly 1 to 6 carbon atoms, including but not limited to linear cyclic, branched, saturated and unsaturated species, such as univalent alkyl, alkenyl, alkynyl and aryl groups e.g. ethyl and phenyl groups.

Unless otherwise indicated, the term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, and others known to a skilled person, and examples of heteroatom-containing alicyclic groups are pyrrolidino, morpholino, piperazino, piperidino, and other known to a skilled person.

Unless otherwise indicated, the term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

Unless otherwise indicated, the term "alkylamino" as used herein intends an alkyl group bound through a single terminal amine linkage; that is, an "alkylamino" may be represented as —NH-alkyl where alkyl is as defined above. A "lower alkylamino" intends a alkylamino group containing 1 to 6 carbon atoms. The term "dialkylamino" as used herein intends two identical or different bound through a common amine linkage; that is, a "dialkylamino" may be represented as —N(alkyl)2 where alkyl is as defined above. A "lower dialkylamino" intends a dialkylamino wherein each alkyl group contains 1 to 6 carbon atoms. Analogously, "alkenylamino", "lower alkenylamino", "alkynylamino", and "lower alkynylamino" respectively refer to an alkenyl, lower alkenyl, alkynyl and lower alkynyl bound through a single terminal amine linkage; and "dialkenylamino", "lower dialkenylamino", "dialkynylamino", "lower dialkynylamino" respectively refer to two identical alkenyl, lower alkenyl, alkynyl and lower alkynyl bound through a common amine linkage. Similarly, "alkenylalkynylamino", "alkenylalkylamino", and "alkynylalkylamino" respectively refer to alkenyl and alkynyl, alkenyl and alkyl, and alkynyl and alkyl groups bound through a common amine linkage.

Unless otherwise indicated, the term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

Unless otherwise indicated, the term "arene", as used herein, refers to an aromatic ring or multiple aromatic rings that are fused together. Exemplary arenes include, for example, benzene, naphthalene, anthracene, and the like. The term "heteroarene", as used herein, refers to an arene in which one or more of the carbon atoms has been replaced by a heteroatom (e.g. O, N, or S). Exemplary heteroarenes include, for example, indole, benzimidazole, thiophene, benzthiazole, and the like. The terms "substituted arene" and "substituted heteroarene", as used herein, refer to arene and heteroarene molecules in which one or more of the carbons and/or heteroatoms are substituted with substituent groups.

Unless otherwise indicated, the terms "cyclic", "cyclo-", and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

Unless otherwise indicated, the terms "halo", "halogen", and "halide" are used in the conventional sense to refer to a chloro, bromo, fluoro or iodo substituent or ligand.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents can include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), aryloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—CO)—X where X is halo), C2-C24 alkylcarbonato (—O—(CO)—O-alkyl), C6-C24 arylcarbonato (—O—(CO)—O-aryl), carboxy (—COOH), carboxylato (COO⁻), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)2), mono-(C5-C24 aryl)-substituted carbamoyl (—(CO)—NH-aryl), di-(C5-C24 aryl)-substituted carbamoyl (—(CO)—N(C5-C24 aryl)2), di-N—(C1-C24 alkyl),N—(C5-C24 aryl)-substituted carbamoyl, thiocarbamoyl (—(CS)—NH2), mono-(C1-C24 alkyl)-substituted thiocarbamoyl (—(CO)—NH (C1-C24 alkyl)), di-(C1-C24 alkyl)-substituted thiocarbamoyl (—(CO)—N(C1-C24 alkyl)2), mono-(C5-C24 aryl)-substituted thiocarbamoyl (—(CO)—NH-aryl), di-(C5-C24 aryl)-substituted thiocarbamoyl (—(CO)—N (C5-C24 aryl)2), di-N—(C1-C24 alkyl),N—(C5-C24 aryl)-substituted thiocarbamoyl, carbamido (—NH—(CO)—NH2), cyano(—C≡N)), cyanato (—O—C≡N), thiocyanato (—S—C≡N), formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, and others known to a skilled person), C2-C20 alkylimino (CR=N(alkyl), where R=hydrogen, C1-C24 alkyl, C5-C24 aryl, C6-C24 alkaryl, C6-C24 aralkyl, and others known to a skilled person), arylimino (—CR=N(aryl), where R=hydrogen, C1-C20 alkyl, C5-C24 aryl, C6-C24 alkaryl, C6-C24 aralkyl, and others known to a skilled person), nitro (—NO2), nitroso (—NO), sulfo (—SO2-OH), sulfonato (—SO2-O⁻), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), C5-C24 arylsulfinyl (—(SO)-aryl), C1-C24 alkylsulfonyl (—SO2-alkyl), C5-C24 arylsulfonyl (—SO2-aryl), boryl (—BH2), borono (—B(OH)2), boronato (—B(OR)2 where R is alkyl or other hydrocarbyl), phosphono (—P(O)(OH)2), phosphonato (—P(O)(O⁻)2), phosphinato (—P(O)(O⁻), phospho (–PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

Unless otherwise indicated, the term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

Unless otherwise indicated, the term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Sletten, E. M., et al., "Bioorthogonal chemistry: fishing for selectivity in a sea of functionality." *Angew Chem Int Ed Engl* 2009 48(38): 6974-6998.
2. Prescher, J. A., et al., "Chemical remodelling of cell surfaces in living animals." *Nature* 2004 430(7002): 873-877.
3. Sawa, M., et al., "Glycoproteomic probes for fluorescent imaging of fucosylated glycans in vivo." *Proc Natl Acad Sci USA* 2006 103(33): 12371-12376.
4. Baskin, J. M., et al., "Copper-free click chemistry for dynamic in vivo imaging." *Proc Natl Acad Sci USA* 2007 104(43): 16793-16797.
5. Zhang, L., et al., "Ruthenium-catalyzed cycloaddition of alkynes and organic azides." *J Am Chem Soc* 2005 127 (46): 15998-15999.
6. Sigma-Aldrich. "Solid Phase Resins." [Accessed Dec. 18, 2012]; Available from: http://www.sigmaaldrich.com/chemistry/drug-discovery/resin-explorer/solid-phase-resins.html#TentaGel %20Resins.

The invention claimed is:

1. A method for sequestering one or more alkyne-presenting molecules possibly present in a matrix, the method comprising:
   providing the matrix sample wherein the one or more alkyne presenting molecules possibly present in the matrix are dispersed;
   providing a sequestration reagent comprising a support presenting one or more azide groups capable of binding the sequestration reagent to one or more alkyne-presenting molecules through click-chemistry; and
   contacting the sequestration reagent with the matrix sample in absence of a treatment of the matrix sample that introduces an alkyne group into the matrix sample prior to the contacting, the contacting being performed for a time and under a condition to allow binding of the sequestration reagent to one or more alkyne-presenting molecules possibly present in the matrix sample through click-chemistry, thus sequestering the alkyne-presenting molecules, when present, from the matrix sample;
   wherein the matrix sample is selected from blood, and urine.

2. The method of claim 1, wherein the sequestration reagent has formula XXXV:

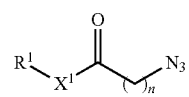

XXXV wherein: $R^1$ is a cross-linked organic polymer; $X^1$ is selected from the group consisting of O, NH, and S; and n is between 4 and 7.

3. The method of claim 1, wherein the contacting is performed by:

dispersing the sequestration reagent in the matrix sample in combination with a copper(0), copper(I) and/or copper(II) compound to provide a mixture; and tumbling the mixture.

4. The method of claim 1, wherein the one or more alkyne-presenting molecules possibly present in the matrix sample comprise a terminal alkyne.

5. The method of claim 4, wherein the terminal alkyne is selected from one of 17α-ethinylestradiol, acetylene, propyne, norethynodrel, and rasagiline.

6. The method of claim 4, wherein the terminal alkyne is 17α-ethinylestradiol.

7. The method of claim 1, wherein the one or more alkyne-presenting molecules possibly present in the matrix sample comprise an internal alkyne group.

8. The method of claim 7, wherein the internal alkyne is selected from one of terbinafine, cicutoxin, oenanthotoxin, falcarinol, efavirenz, calicheamicin, and tariric acid.

9. The method of claim 1, wherein the sequestration reagent has formula XXXVI:

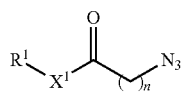

XXXVI wherein: $R^1$ is a cross-linked organic polymer; $X^1$ is selected from the group consisting of O, NH, and S; and n is between 4 and 7; and R1 is a Wang resin, a Rink amide resin, a trityl resin or a chloromethylphenyl polystyrene resin.

10. A method for detecting one or more alkyne-presenting molecules possibly present in a matrix, the method comprising:
providing a matrix sample wherein the one or more alkyne presenting molecules possibly present in the matrix are dispersed;
providing a sequestration reagent comprising a support presenting one or more azide groups capable of binding of the sequestration reagent to one or more alkyne-presenting molecules and a detection reagent through click chemistry; and
contacting the sequestration reagent with the matrix sample in absence of a treatment of the matrix sample that introduces an alkyne group into the matrix sample prior to the contacting, the contacting being performed for a time and under a condition to allow binding of the sequestration reagent to one or more alkyne-presenting molecules possibly present in the matrix sample through click-chemistry, thus sequestering the alkyne-presenting molecules, when present, from the matrix sample;
detecting the one or more alkyne-presenting molecules possibly present in the matrix;
wherein the sequestration reagent has formula XXXVI:

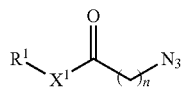

XXXVI wherein: $R^1$ is a cross-linked organic polymer; $X^1$ is selected from the group consisting of O, NH, and S; and n is between 4 and 7; and R1 is a Wang resin, a Rink amide resin, a trityl resin or a chloromethylphenyl polystyrene resin.

11. The method of claim 10, wherein the one or more alkyne-presenting molecules possibly present in the matrix sample comprise a terminal alkyne.

12. The method of claim 11, wherein the terminal alkyne is selected from one of 17α-ethinylestradiol, acetylene, propyne, norethynodrel, and rasagiline.

13. The method of claim 11, wherein the terminal alkyne is 17α-ethinylestradiol.

14. The method of claim 10, wherein the matrix sample is an aqueous or organic solution.

15. The method of claim 10, wherein the matrix sample is selected from blood, urine, drinking water, and agricultural irrigation water.

16. The method of claim 10, wherein the matrix sample is selected from blood, and urine.

17. The method of claim 10, wherein the one or more alkyne-presenting molecules possibly present in the matrix sample comprise an internal alkyne group.

18. The method of claim 17, wherein the internal alkyne is selected from one of terbinafine, cicutoxin, oenanthotoxin, falcarinol, efavirenz, calicheamicin, and tariric acid.

19. A method for sequestering one or more alkyne-presenting molecules possibly present in a matrix, the method comprising:
providing the matrix sample wherein the one or more alkyne presenting molecules possibly present in the matrix are dispersed;
providing a sequestration reagent comprising a support presenting one or more azide groups capable of binding the sequestration reagent to one or more alkyne-presenting molecules through click-chemistry; and
contacting the sequestration reagent with the matrix sample in absence of a treatment of the matrix sample that introduces an alkyne group into the matrix sample prior to the contacting, the contacting being performed for a time and under a condition to allow binding of the sequestration reagent to one or more alkyne-presenting molecules possibly present in the matrix sample through click-chemistry, thus sequestering the alkyne-presenting molecules, when present, from the matrix sample;
wherein the sequestration reagent has formula XXXVI:

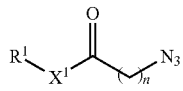

XXXVI wherein: $R^1$ is a cross-linked organic polymer; $X^1$ is selected from the group consisting of O, NH, and S; and n is between 4 and 7; and
R1 is a Wang resin, a Rink amide resin, a trityl resin or a chloromethylphenyl polystyrene resin.

20. The method of claim 19, wherein the matrix sample is an aqueous or organic solution.

21. The method of claim 19, wherein the contacting is performed by: dispersing the sequestration reagent in the matrix sample in combination with a copper(0), copper(I) and/or copper(II) compound to provide a mixture; and tumbling the mixture.

22. The method of claim 19, wherein the matrix sample is selected from drinking water, and agricultural irrigation water.

23. The method of claim 19, wherein the one or more alkyne-presenting molecules possibly present in the matrix sample comprise a terminal alkyne.

24. The method of claim 23, wherein the terminal alkyne is selected from one of 17α-ethinylestradiol, acetylene, propyne, norethynodrel, and rasagiline.

25. The method of claim 23, wherein the terminal alkyne is 17α-ethinylestradiol.

26. The method of claim 19, wherein the one or more alkyne-presenting molecules possibly present in the matrix sample comprise an internal alkyne group.

27. The method of claim 26, wherein the internal alkyne is selected from one of terbinafine, cicutoxin, oenanthotoxin, falcarinol, efavirenz, calicheamicin, and tariric acid.

* * * * *